United States Patent
Ryu et al.

(10) Patent No.: US 8,583,230 B2
(45) Date of Patent: Nov. 12, 2013

(54) SYSTEMS AND METHODS FOR SELECTIVELY LIMITING MULTI-SITE VENTRICULAR PACING DELAYS DURING OPTIMIZATION OF CARDIAC RESYNCHRONIZATION THERAPY PARAMETERS

(75) Inventors: Kyungmoo Ryu, Palmdale, CA (US); Allen Keel, San Francisco, CA (US); Heidi Hellman, Los Angeles, CA (US); Tomas Svensson, Stockholm (SE)

(73) Assignee: Pacesetter, Inc., Sylmar, CA (US)

( * ) Notice: Subject to any disclaimer, the term of this patent is extended or adjusted under 35 U.S.C. 154(b) by 275 days.

(21) Appl. No.: 13/009,404

(22) Filed: Jan. 19, 2011

(65) Prior Publication Data

US 2012/0185012 A1    Jul. 19, 2012

(51) Int. Cl.
*A61N 1/00*    (2006.01)

(52) U.S. Cl.
USPC ............. 607/9; 607/14; 607/15; 607/25

(58) Field of Classification Search
USPC ........................... 607/9, 14, 15, 25
See application file for complete search history.

(56) References Cited

U.S. PATENT DOCUMENTS

| | | | |
|---|---|---|---|
| 6,473,645 B1 | 10/2002 | Levine | |
| 6,512,952 B2 | 1/2003 | Stahmann et al. | |
| 6,628,988 B2 | 9/2003 | Kramer et al. | |
| 6,643,546 B2 | 11/2003 | Mathis et al. | |
| 7,065,400 B2 | 6/2006 | Schechter | |
| 7,139,609 B1 | 11/2006 | Min et al. | |
| 7,248,925 B2 | 7/2007 | Bruhns et al. | |
| 7,590,446 B1 | 9/2009 | Min et al. | |
| 2008/0097536 A1* | 4/2008 | Kramer et al. | 607/9 |
| 2008/0306567 A1 | 12/2008 | Park et al. | |
| 2009/0254140 A1 | 10/2009 | Rosenberg et al. | |
| 2009/0299423 A1 | 12/2009 | Min | |
| 2009/0306732 A1 | 12/2009 | Rosenberg et al. | |
| 2009/0318995 A1 | 12/2009 | Keel et al. | |
| 2010/0145405 A1 | 6/2010 | Min et al. | |
| 2010/0152801 A1 | 6/2010 | Koh et al. | |

OTHER PUBLICATIONS

Leclercq, Christophe MD PhD et al., "A Randomized Comparison of Triple-Site Versus Dual-Site Ventricular Stimulation in Patients With Congestive Heart Failure," JACC. 2008;51(15):1455-1462.

Lenarczyk, Radoslaw et al., "Mid-term outcomes of triple-site vs. conventional cardiac resynchornization therapy: A preliminary study," International Journal of Cardiology. 2009;133:87-94.

(Continued)

*Primary Examiner* — Niketa Patel
*Assistant Examiner* — Mallika D Fairchild

(57) ABSTRACT

Techniques are provided for use with implantable cardiac stimulation devices equipped for multi-site left ventricular (MSLV) cardiac pacing. Briefly, intraventricular and interventricular conduction delays are detected for paced cardiac events. Maximum pacing time delays are determined for use with MSLV pacing where the maximum pacing time delays are set based on the conduction delays to values sufficient to avoid capture problems due to wavefront propagation, such as fusion or lack of capture. MSLV pacing delays are then set to values no greater than the maximum pacing delays and cardiac resynchronization therapy (CRT) is delivered using the MSLV pacing delays. In an example where an optimal interventricular pacing delay (VV) is determined in advance using intracardiac electrogram-based or hemodynamic-based optimization techniques, the optimal value for VV can be used as a limiting factor when determining the maximum MSLV pacing time delays.

14 Claims, 10 Drawing Sheets

(56) References Cited

OTHER PUBLICATIONS

Niazi, Imran K. MD et al., "Dual-Site Left Ventricular Stimulation Provides Better Resynchronization Response Than Conventional Biventricular Stimulation," Heart Rhythm. 2006;3(5):S88—Abstract.

Rosenberg, Stuart P. MS et al., "Simultaneous Linear Multisite LV Stimulation Improves Hemodynamics Above Conventional BV Pacing in Dogs with Rapid Ventricular Pacing Induced Heart Failure," Heart Rhythm. 2008;5(5):S136—Abstract.

* cited by examiner

SYSTEMS AND METHODS FOR SELECTIVELY LIMITING MULTI-SITE VENTRICULAR PACING DELAYS DURING OPTIMIZATION OF CARDIAC RESYNCHRONIZATION THERAPY PARAMETERS

FIELD OF THE INVENTION

The invention generally relates to implantable cardiac stimulation devices such as pacemakers and implantable cardioverter-defibrillators (ICDs) and, in particular, to techniques for determining preferred or optimal multi-site left ventricular (MSLV) pacing delays for use in pacing the heart using cardiac resynchronization therapy (CRT) techniques.

BACKGROUND OF THE INVENTION

CRT pacing seeks to normalize asynchronous cardiac electrical activation and resultant asynchronous contractions associated with congestive heart failure (CHF) by delivering synchronized pacing stimulus to both ventricles of the heart. The stimulus is synchronized to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer at al., entitled "Apparatus and Method for Reversal of Myocardial Remodeling with Electrical Stimulation"; U.S. Pat. No. 6,512,952 to Stahmann et al., entitled "Method and Apparatus for Maintaining Synchronized Pacing"; U.S. Pat. No. 7,065,400 to Schechter, entitled "Method and Apparatus for Automatically Programming CRT Devices"; and U.S. Patent Application 2008/0306567 of Park et al., entitled "System and Method for Improving CRT Response and Identifying Potential Non-Responders to CRT Therapy."

CRT usually involves pacing from the right ventricular (RV) apex, the transvenous LV, typically in the lateral or postero-lateral vein, and the right atrium (RA). Recent studies have suggested that biventricular (BiV) pacing from two LV sites results in an improved clinical outcome in CRT patients, likely due to improved hemodynamic response from dual-LV pacing, in comparison with conventional BiV pacing. A study conducted by Leclercq et al., referred to as the TRIP-HF study (Leclercq et al., "A randomized comparison of triple-site vs. dual-site ventricular stimulation in patients with CHF" JACC 2008; 51:1455-62), demonstrated that CRT with one RV and two LV leads was safe and associated with significantly more reverse remodeling (as assessed by LV ejection fraction (EF) and LV end-systolic volume/diameter) than conventional BiV stimulation. A study conducted by Lenarczyk et al., "Mid-term outcomes of triple-site vs. conventional cardiac resynchronization therapy: A preliminary study," Intern. Journal of Cardiology 2009; 133:87-94, has shown that after three months of CRT, triple-site (TRIV) pacing was associated with a more significant New York Heart Association (NYHA) class reduction, increase is VO2 max and six-minute walk distance than conventional CRT. The response rate in the TRIV group was 96.3% vs. 62.9% in the conventional group, and TRIV stimulation was found to be an independent predictor of response to CRT. Moreover, Niazi et al., "Dual-site left ventricular stimulation provides better resynchronization response than conventional biventricular stimulation" Heart Rhythm 2006; 3(5):S88 have shown that CRT with simultaneous dual LV site pacing produced a significantly larger increase in maximum change in LV pressure (dP/dtMax) compared to BiV CRT with a single LV site pacing. Rosenberg et al., "Simultaneous Linear Multisite LV Stimulation Improves Hemodynamics Above Conventional BiV Pacing in Dogs with Rapid Ventricular Pacing Induced Heart Failure" Heart Rhythm 2008; 5(5):S136) recently evaluated the hemodynamic effects of multisite LV pacing from a single coronary sinus (CS) branch in a rapid RV pacing-induced HF canine model. They reported that simultaneous MSLV pacing from a single CS branch improves LV hemodynamics compared to single-site LV pacing. In the aforementioned studies, the pulses in the dual-LV pacing were delivered simultaneously with no intraventricular delay (i.e. no LV-to-LV delay).

MSLV pacing systems have been proposed that offer the flexibility of varying an interventricular RV-to-LV pacing delay (RVLV) as well as an intraventricular LV-to-LV pacing delay (LVLV). However, issues can arise when setting these or similar pacing delays. In particular, circumstances can arise where the delays are set too long such that propagation of electrical depolarization wavefronts from other pacing sites can interfere with MSLV pacing. In particular, the depolarization wavefronts can prevent capture of MSLV pacing pulses delivered at sites in the LV or can fuse with events paced at those sites. In either case, inappropriate or ineffective CRT pacing can result. Also, circumstances can arise where the pacing might be proarrhythmic.

Accordingly, it would be desirable to prevent inappropriate or ineffective CRT due to these issues and it is to this end that the invention is primarily directed.

SUMMARY OF THE INVENTION

In an exemplary embodiment of the invention, a method is provided for use with an implantable cardiac stimulation device equipped for MSLV pacing using a multi-pole (or "multi-electrode") LV lead in combination with an RV lead. Briefly, intraventricular and interventricular conduction delays (or "activation" delays) are detected for paced cardiac events. Maximum permissible pacing time delays are determined for use with MSLV pacing, wherein the maximum pacing time delays are set based on the conduction delays to values sufficient to avoid capture problems due to wavefront propagation, such as fusion or lack of capture. MSLV pacing delays are set to values no greater than the maximum permissible pacing delays and ventricular pacing is then controlled to deliver a set of pulses using the MSLV pacing delays.

In an illustrative example, the device is a pacemaker or ICD equipped to deliver CRT. The device provides for two programmable MSLV pacing delays (IED#1 and IED#2) for use with one or two MSLV pacing sequences (Seq#1 and Seq#2) that may be programmed by a clinician. (It should be understood that devices can accommodate additional programmable delays and additional pacing sequences. The present example is merely illustrative.) When using the first MSLV pacing sequence (Seq#1), an RV pulse is followed by an LV1 pacing pulse and then by an LV2 pacing pulse, wherein LV1 and LV2 represent different LV pacing locations. For example, LV1 may represent a site defined by a pair of relatively distal. LV electrodes (D1 and M2); whereas LV2 may represent a site defined by a pair of relatively proximal LV electrodes (M3 and P4.) The first delay (IED#1) is applied between the RV and LV1 pulses and the second delay (IED#2) is applied between the LV1 and LV2 pulses. In contrast, when using the second MSLV pacing sequence (Seq#2), the first delay (IED#1) is applied between the LV1 and LV2 pulses and the second delay (IED#2) is applied between the LV2 and RV pulses. That is:

$$RV \rightarrow IED\#1 \rightarrow LV1 \rightarrow IED\#2 \rightarrow LV2 \quad (SEQ\ \#1)$$

$$LV1 \rightarrow IED\#1 \rightarrow LV2 \rightarrow IED\#2 \rightarrow RV \quad (SEQ\ \#2)$$

In an example where Seq#1 is used, the first delay (IED#1) is programmed to a value no greater than a maximum programmable first delay (IED#1_max), which is initially set to the lesser of an initial IED#1_max value (typically 80 ms) and a first paced interventricular conduction delay (RVLV1) minus a fusion avoidance offset. The offset is set to a value (typically 5 ms) sufficient to avoid possible fusion with a paced depolarization wavefront so as to better ensure capture of the myocardium with the following pacing pulse. The second delay (IED#2) is programmed to a value no greater than a maximum programmable second delay (IED#2_max,) which is initially set to the lesser of an initial IED#2_max value (typically 50 ms) and a paced intraventricular conduction delay (LVLV) minus the fusion avoidance offset. In one particular example:

$$IED\#1\_max=Min(80\ ms, RVLV1-5\ ms)$$

$$IED\#2\_max=Min(50\ ms, LVLV-5\ ms).$$

The system then operates to lower the values for IED#1_max and IED#2_max, if warranted, to ensure that the IED#1 and IED#2 values used during CRT pacing do not result in aforementioned capture problems, such as fusion or lack of capture. More specifically, if the combined duration of IED#1_max and IED#2_max is found to be greater than or equal to an RVLV2 delay minus the offset, the device decrements either or both of IED#1_max and IED#2_max until the combined duration is no longer greater than or equal to RVLV2 minus the offset. In an example where a preferred interventricular pacing delay (VV_opt) is determined in advance using intracardiac electrogram (IEGM)-based or hemodynamic-based optimization techniques, the value for VV_OPT can be used as a limiting factor. (Herein, in at least some examples, VV_opt represents a preferred or optimal value for an interventricular (RVLV) pacing delay for applying between an RV pulse and an LV pulse.) For example, if the combined duration of IED#1_max and IED#2_max is found to be greater than or equal to Min(RVLV2-the offset, VV_OPT), the device decrements IED#1_max and/or IED#2_max until the combined duration is no longer greater than or equal to Min(RVLV2-the offset, VV_OPT). In another example, the device sets IED#1_max=Min(initial IED#1_max, RVLV2-the offset, VV_opt) in cases where the combined duration of IED#1_max and IED#2_max is found to be greater than or equal to Min(RVLV2-the offset, VV_opt.)

In an example where Seq#2 is used, the first delay (IED#1) is set to the lesser of the initial IED#1_max value (80 ms) and a paced intraventricular conduction delay (LVLV) measured within the patient minus the fusion avoidance offset. The second delay (IED#2) is set to the lesser of the initial IED#2_max value (50 ms) and a second intrinsic intraventricular conduction delay (LV2RV) measured within the patient minus the fusion avoidance offset. In one particular example:

$$IED\#1\_max=Min(80\ ms, LVLV-5\ ms)$$

$$IED\#2\_max=Min(50\ ms, LV2RV-5\ ms).$$

If the combined duration of IED#1_max and IED#2_max is found to be greater than or equal to an LV1RV delay minus the offset, then the device decrements either or both of IED#1_max and IED#2_max until the combined duration is no longer greater than or equal to LV1RV minus the offset. In an example where a preferred interventricular pacing delay (VV_opt) has been determined, the value for VV_opt can again be used as a limiting factor. For example, if the combined duration of IED#1_max and IED#2_max is found to be greater than or equal to Min(LV1RV-the offset, VV_opt) then the device decrements either or both of IED#1_max and IED#2_max until the combined duration is no longer greater than or equal to Min(LV1RV-the offset, VV_opt). In another example, the device sets IED#1_max=Min(initial IED#1_max, LV1RV-the offset, VV_opt) in cases where the combined duration of IED#1_max and IED#2_max is found to be greater than or equal to Min(LV1RV-the offset, VV_opt).

In the exemplary implementations, once the maximum values (IED#1_max and IED#2_max) have been lowered using the aforementioned procedures, the device then inputs or otherwise determines optimal values for IED#1 and IED#2 for use in CRT pacing that do not exceed the maximum values. For example, if the implanted device is in communication with an external programmer, the device can input clinician-specified values for IED#1 and IED#2 from among a range of programmable values that do not exceed the adjusted values for IED#1_max and IED#2_max. If the system is equipped to perform an automatic optimization search for determining optimal values for IED#1 and IED#2, the system performs the search using a range of values bounded by the adjusted values for IED#1_max and IED#2_max. In many cases, by lowering the values for IED#1_max and IED#2_max, the amount of time needed to search for optimal values for IED#1 and IED#2 can be greatly reduced. Thus, in addition to avoiding the aforementioned capture problems during CRT pacing, as well as avoiding possible proarrhythmic pacing, the techniques of the invention can also reduce the amount of time needed to perform MSLV delay optimization searches.

Although described primarily with respect to implementations having a multi-pole LV electrode, aspects of the invention are also applicable, where appropriate, to multi-pole RV leads or multi-pole atrial leads as well. Note also that, herein, by "interventricular," it is meant that the delays are between LV sites and RV sites. Delays between different LV sites are referred to as LV "intraventricular" delays or LV "interelectrode" delays. Also, although summarized with respect to examples where only two programmable MSLV delays are used in conjunction with two pacing sequences, the principles of the invention are broadly applicable to systems where more MSLV delays/sequences are used or different MSLV delays/sequences are employed.

System and method implementations of various exemplary techniques are presented herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
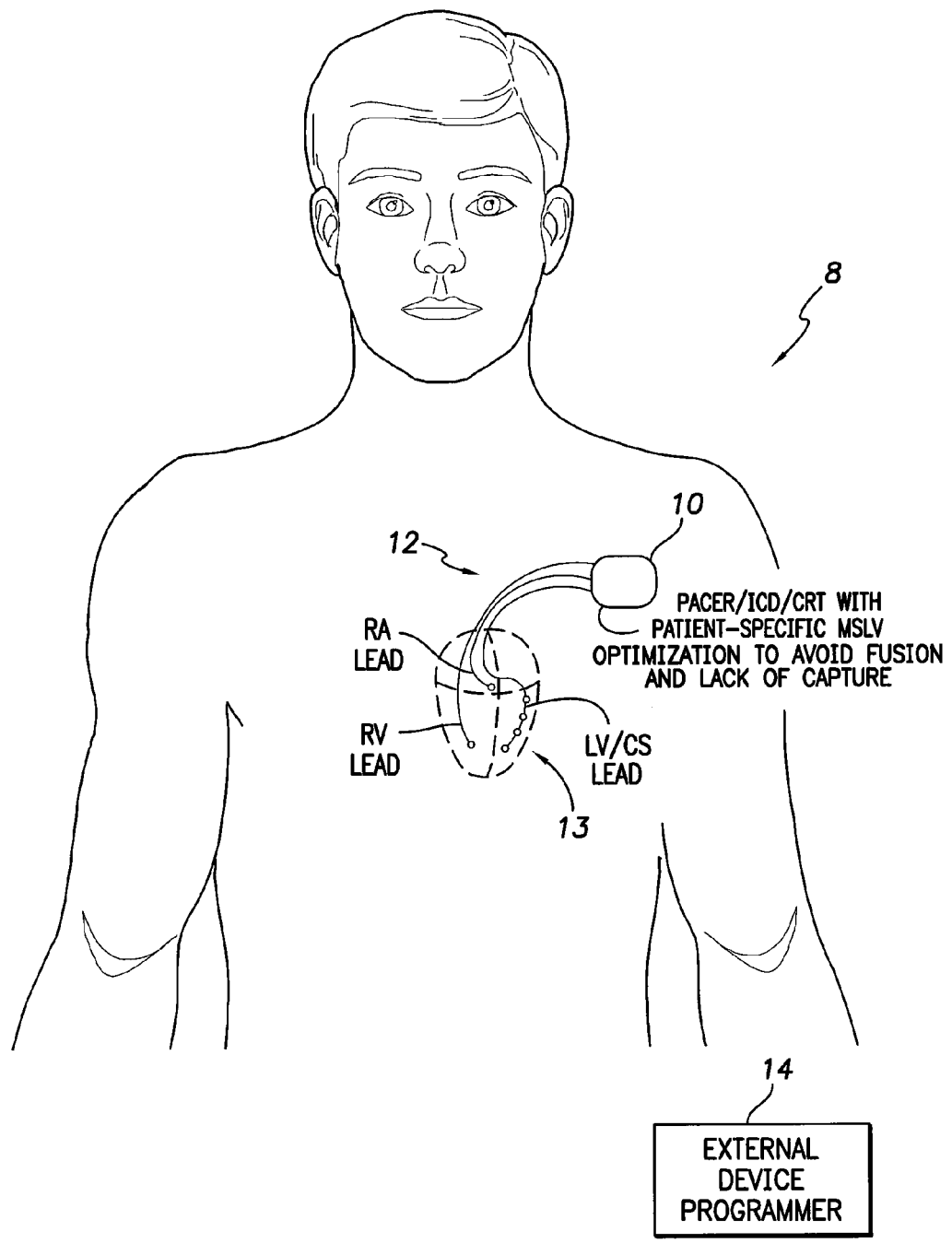
FIG. 1 illustrates components of an implantable medical system having a pacemaker or ICD equipped with a patient-specific MSLV optimization system operative to selectively limit maximum MSLV pacing delays to avoid capture problems during CRT due to wavefront propagation.

FIG. 1 illustrates an implantable medical system 8 equipped for patient-specific MSLV optimization to avoid fusion and lack of capture during CRT pacing. The medical system 8 includes a pacer/ICD/CRT 10 or other cardiac rhythm management device equipped with one or more cardiac sensing/pacing leads 12 implanted on or within the heart of the patient, including a multi-pole LV lead implanted via the CS. In FIG. 1, a stylized representation of the set of leads is provided. To illustrate the multi-pole configuration of the LV lead, a set of electrodes 13 is shown distributed along the LV lead. The RV and RA leads are each shown with a single electrode, though each of those leads may include additional electrodes as well, such as tip/ring electrode pairs. Still further, the LV lead can also include one or more left atrial (LA) electrodes mounted on or near the LA via the CS. See FIG. 8 for a more complete and accurate illustration of various exemplary leads. Although identified as a pacer/ICD/CRT in FIG. 1, it should be understood that device 10 can be any suitably-equipped implantable medical device, such as a standalone pacemaker, ICD, or CRT device, including CRT-D and CRT-P devices. In the following, for brevity, device 10 will be referred to simply as a pacer/ICD.

In some implementations, the pacer/ICD itself performs the patient-specific MSLV optimization based on electrocardiac signals sensed using its leads. In other implementations, the device transmits features of the electrocardiac signals to an external device programmer 14 that performs the optimization. That is, the device programmer determines optimal MSLV pacing parameters for use with the particular patient, which are then programmed into the pacer/ICD via wireless telemetry. Other external devices might instead be used to perform the optimization, such as bedside monitors or the like. In some embodiments, the device programmer or bedside monitor is directly networked with a centralized computing system. The centralized system may include such systems as Merlin.Net of St. Jude Medical, which may be used in conjunction with bedside monitors or similar devices such as the HouseCall™ remote monitoring system or the Merlin@home systems, also of St. Jude Medical.

In the following examples, it is assumed that the pacer/ICD performs the patient-specific MSLV optimization using on-board components. An example where the external programmer performs the optimization is described below with reference to FIG. 10.

Overview of Patient-Specific MSLV Optimization

Figure 2:
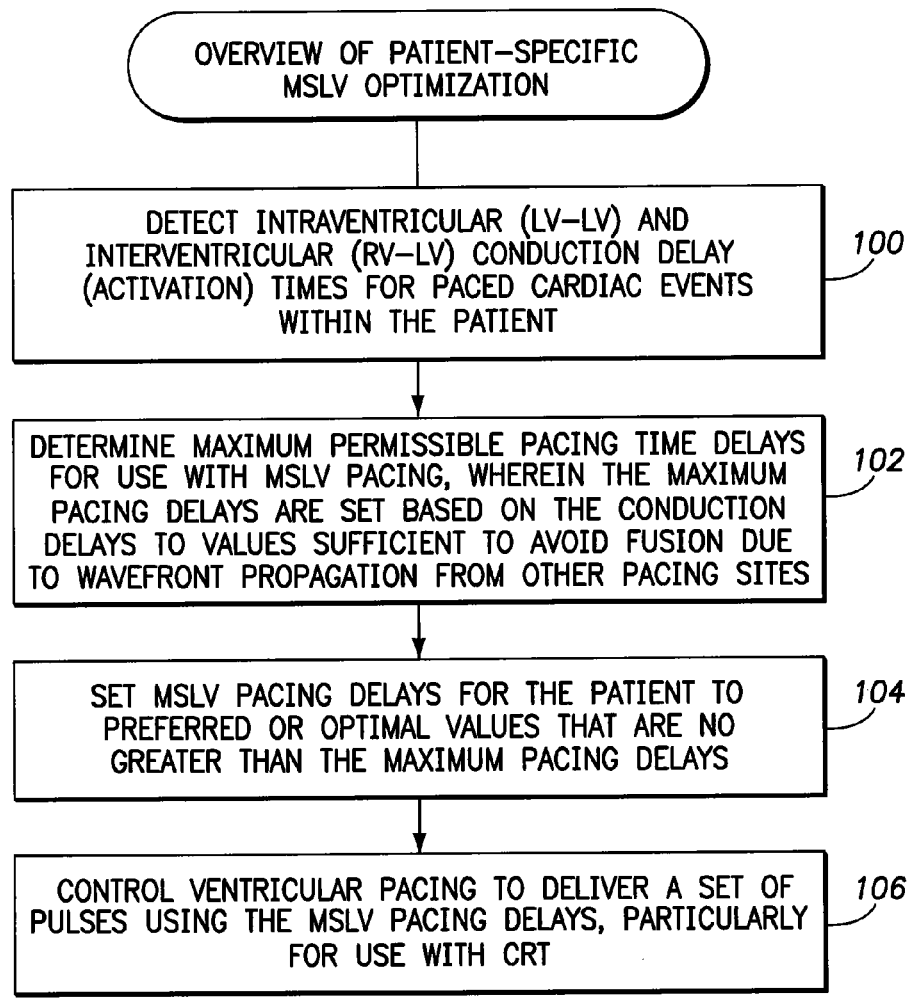
FIG. 2 is a flowchart providing an overview of a technique for limiting maximum pacing delays during MSLV optimization to avoid capture problems, which may be performed by the system of FIG. 1.
Figure 3:
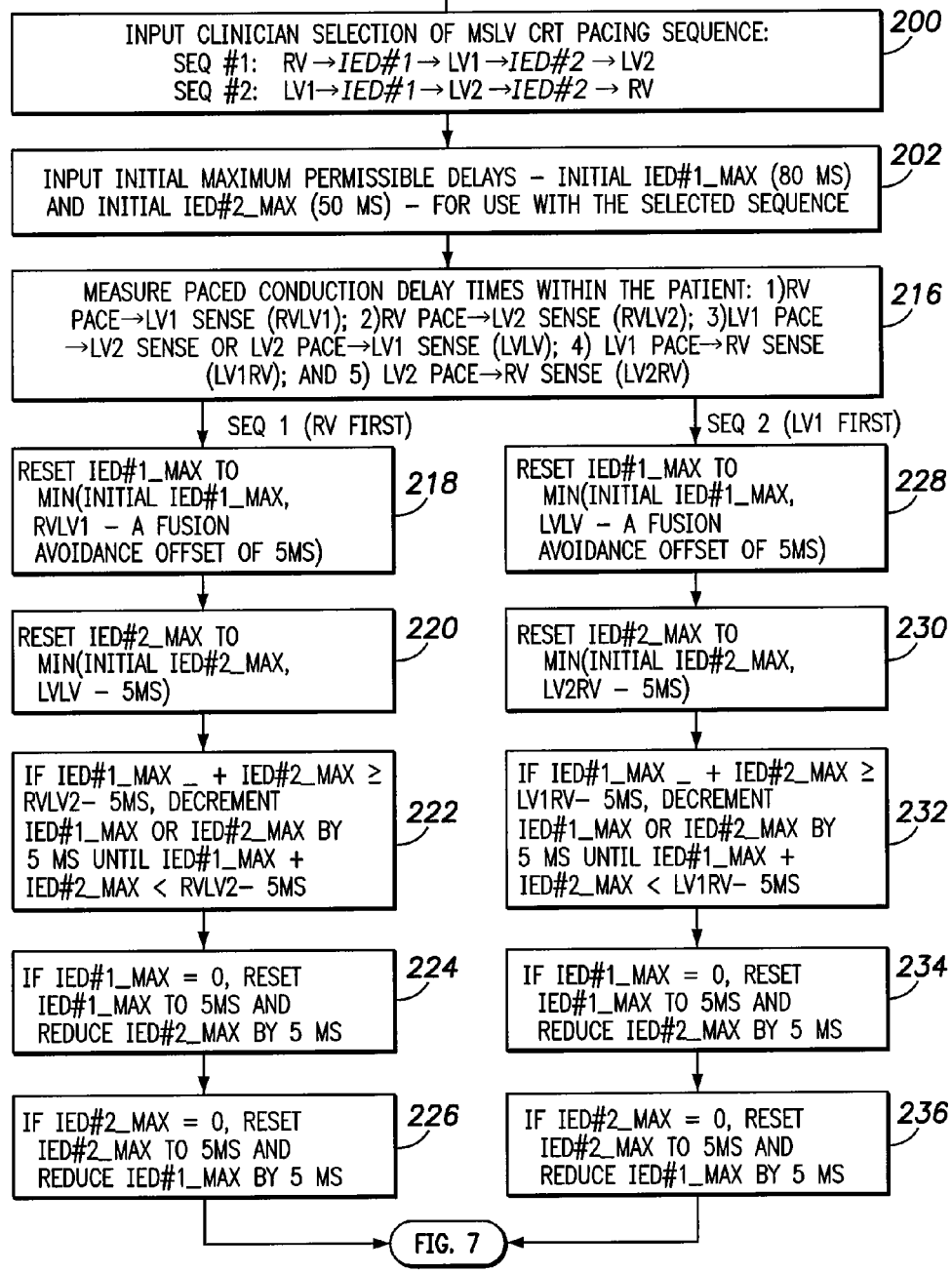
FIG. 3 is a flowchart illustrating an exemplary implementation of the technique of FIG. 2 for use with an MSLV system that allows for two programmable MSLV pacing delays for use with two pacing sequences.

FIG. 2 broadly summarizes a general technique that may be exploited by the pacer/ICD of FIG. 1 for limiting maximum programmable pacing delays during MSLV optimization to avoid capture problems due to wavefront propagation. Beginning at step 100, the pacer/ICD detects interventricular (RV-LV) and intraventricular (LV-LV) conduction delays (i.e. activation times) for paced cardiac events within the patient. This may be performed by examining IEGM signals sensed by the leads of the device while selectively delivering pacing pulses using the electrodes of those leads. In some examples, delays can be detected between each and every possible combination of electrodes of the lead system. Typically, however, it is sufficient to measure a much smaller set of conduction delays, as will be discussed below. At step 102, the device determines maximum permissible pacing time delays for use with MSLV pacing, wherein the maximum pacing time delays are set based on the detected conduction delays to values sufficient to avoid fusion or lack of capture due to wavefront propagation from other pacing sites. In this regard, if the MSLV pacing delay between a particular pair of pacing sites is set too long, a paced depolarization wavefront (i.e. an evoked response wavefront) triggered at a first site will propagate to the second site before pacing is delivered at the second site. As a result, the second pacing pulse might fuse with the incoming wavefront or might not be captured at all. In either case, proper MSLV pacing is not delivered, possibly interfering with the efficacy of CRT and/or reducing cardiac performance. In some cases, the resulting pacing might be proarrhythmic. By setting the maximum pacing delays to values sufficient to avoid fusion or lack of capture, appropriate MSLV pacing can be achieved.

At step 104, the device then sets MSLV pacing delays for the patient to preferred or optimal values that are no greater than the maximum permissible pacing delays. As will be explained further below, in one example, an optimization search is performed to find optimal MSLV pacing delay values for use with CRT from within a range of values that do not exceed the maximum pacing delays. In another example, the maximum MSLV delays are transmitted to an external device programmer for display thereon for clinician review. The clinician then selects MSLV pacing delays from within a range of acceptable values that do not exceed the maximum pacing delays. The clinician selections are then transmitted to the pacer/ICD and stored in its memory systems for use in controlling MSLV pacing. In any case, at step 106, the pacer/ICD controls ventricular pacing to deliver a set of pulses using the MSLV pacing delays, particularly for use with CRT. Additionally, atrial pacing pulses can be delivered as well. Numerous other device functions can also be performed that are not explicitly listed within the figure.

For CRT techniques, in addition to the patent documents listed above, see: U.S. Patent Application 2010/0152801 of Koh et al., entitled "Cardiac Resynchronization Therapy Optimization Using Vector Measurements Obtained from Realtime Electrode Position Tracking"; U.S. Published Patent Application 2009/0318995 of Keel et al., entitled "Cardiac Resynchronization Therapy Optimization using Mechanical Dyssynchrony and Shortening Parameters from Realtime Electrode Motion Tracking"; U.S. Patent Application 2009/0306732 of Rosenberg et al., entitled "Cardiac Resynchronization Therapy Optimization using Electromechanical Delay from Realtime Electrode Motion Tracking"; and U.S. Patent Application 2009/0254140 of Rosenberg et al., entitled "Cardiac Resynchronization Therapy Optimization using Parameter Estimation From Realtime Electrode Motion Tracking."

Exemplary Techniques for Limiting the Maximum Programmable MSLV Delays

FIGS. 3-7 illustrate exemplary techniques for use with an MSLV system that uses two programmable delays (IED#1 and IED#2) for use with one of two programmable pacing sequences (SEQ#1 and SEQ#2.) At step 200, the device inputs a clinician selection of the particular MSLV CRT pacing sequence to be used via wireless telemetry from an external device programmer (or by retrieving the selection from device memory if it has already been programmed into the device.) The first programmable sequence specifies that the RV is paced first, followed by a first LV site (LV1) after the IED#1 delay and then a second LV site (LV2) after the IED#2 delay. The RV site might be, for example, located near the RV apex (using a pair of distal tip/ring RV electrodes implanted near that location or using other suitable pairs of electrodes such as RV tip/RV coil or R tip/can.) The first LV site might be, for example, located near the LV apex (using a pair of distal LV electrodes implanted near that location); whereas the second LV site might be located closer to the coronary sinus (using a pair of more proximally located LV electrodes.) In contrast, the second programmable sequence specifies that the LV1 is paced first, followed by LV2 and then the RV site. The two sequences and the pacing delays may be represented as follows:

RV→IED#1→LV1→IED#2→LV2   SEQ #1:

LV1→IED#1→LV2→IED#2→RV   SEQ #2:

At step 202, the device inputs initial values for maximum permissible delays—initial IED#1_max and initial IED#2_max—for use with the selected sequence. These values can be pre-programmed into the device. In an exemplary implementation, the initial value of IED#1_max is set to 80 ms, whereas the initial value for IED#2_max is set to 50 ms. These values may depend on the particular lead used. In the examples described herein, the LV lead is a Model 1458Q "Quartet" Quadpole lead, provided by St. Jude Medical.

Figure 4:
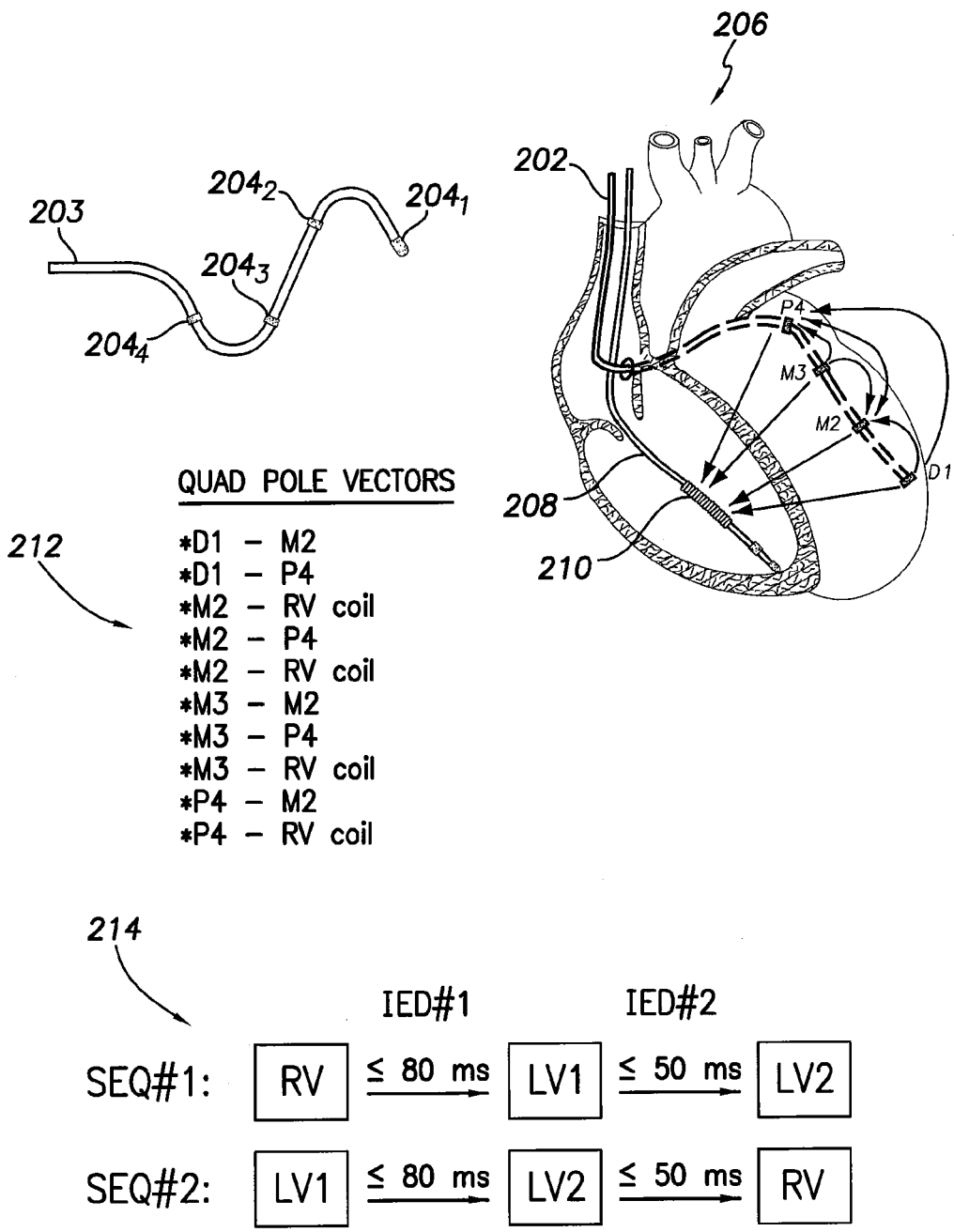
FIG. 4 illustrates exemplary quadripole vectors and pacing delays for use with the techniques of FIG. 3.

FIG. 4 illustrates the two exemplary sequences along with graphical representations of leads and pacing vectors. An exemplary quadripole LV lead 203 is shown along with its four electrodes, denoted $204_1$-$204_4$. (Quadripole leads may also be referred to as "quadrapole" or "quadpole" leads.) The electrodes are also identified herein by alphanumeric designators: D1 for the LV tip electrode $204_1$; M2 for a first LV ring electrode $204_2$; M3 for a second LV ring electrode $204_3$; and P4 for a third LV ring electrode $204_4$. A graphic illustration 206 of a patient's heart shows LV lead 202 along with an RV lead 208 having a coil electrode 210. A set of ten Quad Pole pacing vectors that employ these electrodes are shown by way of list 212. As can be seen, some of the vectors are intraventricular LV vectors (vectors between two LV electrodes); whereas others are interventricular vectors (vectors between an LV electrode and the RV coil.) Block diagram 214 illustrates the two pacing sequences and the IED#1 and IED#2 pacing delays therebetween, including the initial maximum values for those delays of 80 ms and 50 ms, respectively.

When using these sequences, problems can arise if IED#1 and IED#2 are not set properly. More specifically, when using Seq#1 (i.e. RV→LV1→LV2), if the RV to LV1 delay (i.e. IED#1) is programmed at 30 ms, then RV to LV2 conduction should be greater than 30 ms. However, the wavefront from RV pace can travel to LV2 faster than the programmed time (IED#1) resulting in possible fusion or lack of capture at LV2. This is also dependant on RV lead position (RV apex, RV septum, or RV outflow tract (RVOT)) and on LV lead position (anterior, anterior-lateral, lateral, postero-lateral, posterior, apex, mid-basal, or basal.) When using Seq#2, (i.e. LV1→LV2→RV), if LV1 to LV2 is programmed at 40 ms, LV1→RV conduction should be greater than 40ms. However, the wavefront from LV1 pace can travel to RV faster than the programmed time (IED#1) resulting in possible fusion or delivery of unnecessary pulse at RV. As a result, CRT might be ineffective or incomplete. The unnecessary pacing at RV might be proarrhythmic if it is delivered at a refractory period of the RV electrode location. Also, any unnecessary pacing can needlessly drain the device battery.

Returning to FIG. 3, the device performs a series of steps to avoid these capture-related problems. At step 216, the device measures the following paced conduction delay times within the patient: 1) RV pace→LV1 sense (RVLV1); 2) RV pace→LV2 sense (RVLV2); 3) LV1 pace→LV2 sense or LV2 pace→LV1 sense (LVLV); 4) LV1 pace→RV sense (LV1RV); and 5) LV2 pace→RV sense (LV2RV.) These values will be used (if needed) to lower the values for IED#1_max and IED#2_max to avoid fusion or lack or capture. Note that the choice or whether to measure LV1 pace→LV2 sense or LV2 pace→LV1 sense for use as the LVLV value is arbitrary since the resulting conduction delay value should be substantially the same.

Next, assuming that Seq#1 has been selected, the device, at step 218, resets IED#1_max to Min(initial IED#1_max, RVLV1-a fusion avoidance offset) where the fusion avoidance offset is set, in this example, to 5 ms. (It is noted that, if the device platform permits it, the offset might instead be set to smaller values, including zero.) For the case where initial IED#1_max is set to 80 ms and the offset is 5 ms, the device thereby resets IED#1_max to Min(80 ms, RVLV1-5 ms.) At step 220, the device resets IED#2_max to Min(initial IED#2_max, LVLV-the offset.) For the case where initial IED#2_max is set to 50 ms and the offset is 5 ms, the device thereby resets IED#2_max to Min(50 ms, LVLV-5 ms.) Once the values have been reset, the device checks to determine if the values need to be adjusted further to avoid anomalous situations. At step 222, the device checks to determine if IED#1_max+IED#2_max≥RVLV2-the offset. If so, the device decrements IED#1_max or IED#2_max by 5 ms (or some other suitable decrement value) until IED#1_max+IED#2_max<RVLV2-5 ms. Then, at step 224, if IED#1_max is now zero (or negative), the device resets IED#1_max to 5 ms (or some other minimum value) and reduces IED#2_max by 5 ms (or some other suitable decrement value.) Likewise, at step 226, if IED#2_max is now zero (or negative), the device resets IED#2_max to 5 ms (or some other minimum value) and reduces IED#1_max by 5 ms (or some other suitable decrement value.) Having reset the values for IED#1_max and IED#2_max for Seq#1, the device then proceeds to the steps of FIG. 7, which will be discussed below, where the IED#1_max and IED#2_max values are used to limit the range of values for IED#1 and IED#2.

On the other hand, assuming that Seq#2 has been instead selected, the device, at step 228, resets IED#1_max to Min (initial IED#1_max, LV1LV–the offset) where the fusion avoidance offset is again set, in this example, to 5 ms. At step 230, the device resets IED#2_max to Min(initial IED#2_max, LV2RV–the offset.) At step 232, the device checks to determine if IED#1_max+IED#2_max≥LV1RV–the offset. If so, the device decrements IED#1_max or IED#2_max by 5 ms (or some other suitable decrement value) until IED#1_max+IED#2_max<LV1RV–5 ms. Then, at step 234, if IED#1_max is now zero (or negative), the device resets IED#1_max to 5 ms (or some other minimum value) and reduces IED#2_max by 5 ms (or some other suitable decrement value.) Likewise, at step 236, if IED#2_max is now zero (or negative), the device resets IED#2_max to 5 ms (or some other minimum value) and reduces IED#1_max by 5 ms (or some other suitable decrement value.) Having reset the values for IED#1_max and IED#2_max for Seq#2, the device then proceeds to the steps of FIG. 7, discussed below, where the IED#1_max and IED#2_max values are used to limit the range of values for IED#1 and IED#2.

Figure 5:
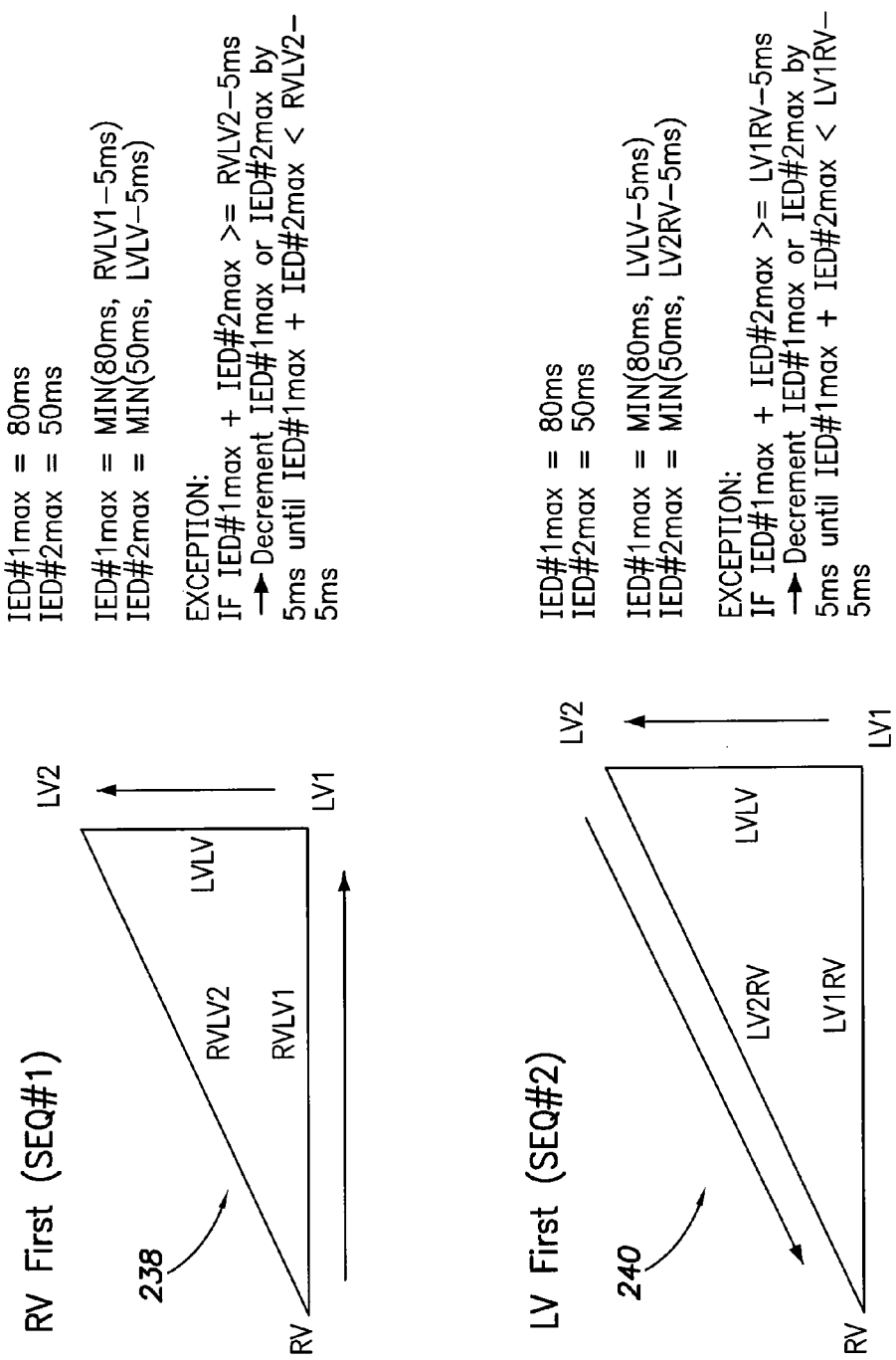
FIG. 5 illustrates exemplary maximum MSLV delay calculation equations for use with the techniques of FIG. 3.

FIG. 5 graphically illustrates the pacing delays used for the two sequences (Seq#1 and Seq#2.) A first graph 238 schematically illustrates the RV, LV1 and LV2 pacing sites and the pacing delays therebetween for use with Seq#1. Alongside, a summary of the procedure for adjusting IED#1_max and IED#2_max for use with Seq#1 is provided. A second graph 240 schematically illustrates for use with Seq#2. Again, a summary of the procedure for adjusting IED#1_max and IED#2_max for use with Seq#2 is also illustrated.

Figure 6:
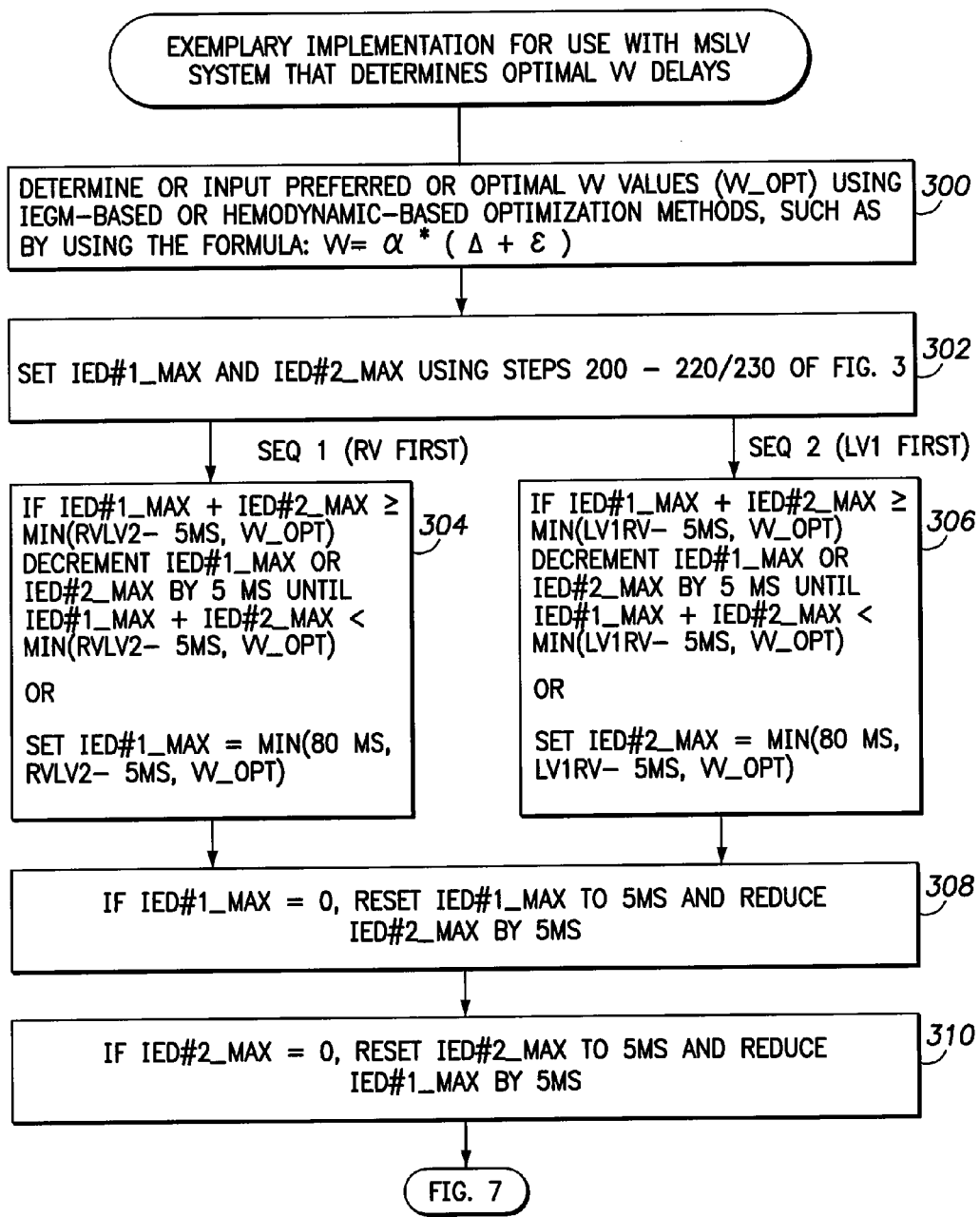
FIG. 6 is a flowchart exemplary techniques for use with the method of FIG. 3 in implementations where optimal VV delays are initially determined prior to setting of individual MSLV pacing delays.

Turning now to FIG. 6, an alternative technique is described for adjusting IED#1_max and IED#2_max for use in implementations where optimal values for VV are determined before values for IED#1 and IED#2 are set. As noted above, VV_opt represents a preferred or optimal value for an interventricular (RVLV) pacing delay for use between an RV pulse (e.g. delivered using RVtip/RVring electrodes) and an LV pulse (e.g. delivered using the electrodes of LV1.) Note that any of a variety of suitable bipolar or unipolar configurations can be used, depending upon the particular embodiment.) At step 300, the device determines or inputs preferred or optimal VV values (VV_opt) using IEGM-based or hemodynamic-based optimization methods. In some cases, the value for VV_opt is determined by the device (assuming it is equipped to perform such optimization.) In other cases, the value for VV_opt is input from an external system, such as a device programmer, which has performed the optimization.

In this regard, clinical studies related to cardiac pacing have shown that an optimal atrioventricular pacing delay (e.g., AV delay or PV delay) and/or an optimal interventricular pacing delay (e.g., VV_opt) can improve cardiac performance. The following patents and patent applications set forth various systems and methods for allowing a pacemaker, ICD or other cardiac rhythm management (CRM) device to determine and/or adjust preferred or optimal AV/PV/VV pacing delays based on IEGMs and/or hemodynamic parameters: U.S. patent application Ser. No. 10/703,070, filed Nov. 5, 2003, entitled "Methods for Ventricular Pacing" U.S. patent application Ser. No. 10/974,123, filed Oct. 26, 2004 U.S. patent application Ser. No. 10/986,273, filed Nov. 10, 2004, now U.S. Pat. No. 7,590,446; U.S. patent application Ser. No. 10/980,140, filed Nov. 1, 2004 U.S. patent application Ser. No. 11/129,540, filed May 13, 2005 U.S. patent application Ser. No. 11/952,743, filed Dec. 7, 2007. See, also, U.S. patent application Ser. No. 12/328,605, filed Dec. 4, 2008, entitled "Systems and Methods for Controlling Ventricular Pacing in Patients with Long IntraAtrial Conduction Delays," now U.S. Patent Application 2010/0145405; and U.S. patent application Ser. No. 12/132,563, filed Jun. 3, 2008, entitled "Systems and Methods for determining IntraAtrial Conduction Delays using Multi-Pole Left Ventricular Pacing/Sensing Leads," now U.S. Patent Application 2009/0299423. See, further, U.S. Pat. No. 7,248,925 to Bruhns et al., entitled "System and Method for Determining Optimal Atrioventricular Delay based on Intrinsic Conduction Delays." At least some of the techniques are implemented within the QuickOpt™ systems of St. Jude Medical.

In particular, techniques are set forth within at least some of these patent documents for exploiting various interatrial and interventricular conduction delays to determine preferred or optimal AV/PV/VV pacing delays. In at least some examples, the implanted device (or an external programming device in communication with the implanted device) performs a series of tests to determine intrinsic AV/PV/VV conduction delays from which optimal pacing delays are determined. For example, an "A sense" test may be performed to detect intrinsic intraatrial delays from which preferred AV/PV pacing delays are determined. A "V sense" test may be performed to detect intrinsic ventricular events from which an intrinsic interventricular conduction delay ($\Delta$) is determined. An "RV pace" test and a separate "LV pace" test may be performed to detect paced interventricular conduction delays (IVCD_RL and IVCD_LR, respectively) from which an intrinsic interventricular correction term ($\epsilon$) is determined. An optimal VV delay for use in biventricular pacing is then set based on $\Delta$ and $\epsilon$ using, for example, $VV=\alpha*(\Delta+\epsilon)$, where $\alpha$ is set to 0.5 (or other suitable coefficient value) and where $\epsilon=IVCD\_LR-IVCD\_RL$.

At step 302, the device then sets or resets IED#1_max and IED#2_max using the techniques of steps 200-220/230 of FIG. 4. That is, for Seq#1, IED#1_max and IED#2_max are reset in accordance with steps 218 and 220 of FIG. 4. For Seq#2, IED#1_max and IED#2_max are reset in accordance with steps 228 and 230 of FIG. 4. Then, if Seq#1 has been selected (i.e. RV first), the device further adjusts the values of IED#1_max and IED#2_max, if needed, based on VV_opt. More specifically, in one example, if IED#1_max+IED#2_max≥Min(RVLV2–5 ms, VV_opt), the device decrements IED#1_max or IED#2_max by 5 ms (or other decrement value) until IED#1_max+IED#2_max<Min(RVLV2–5 ms, VV_opt). That is, instead of performing step 222 wherein RVLV2 is used as the only limiting value, the device also uses VV_opt as a limiting value. Alternatively, the device sets IED#1_max=Min(80 ms, RVLV2–5 ms, VV_opt), where 80 ms is an exemplary value for the initial IED#1_max value and 5 ms is an exemplary offset value.

Conversely, if Seq#2 has instead been selected (i.e. LV1 first), the device adjusts the values of IED#1_max and IED#2_max, in one example, as follows. If IED#1_max+IED#2_max>Min(LV1RV–5 ms, VV_opt), the device decrements IED#1_max or IED#2_max by 5 ms (or other decrement value) until IED#1_max+IED#2_max<Min(LV1RV–5 ms, VV_opt). That is, instead of performing step 232 wherein LV1RV is used the only limiting value, the device also uses VV_opt as a limiting value. Alternatively, the device sets IED#1_max=Min(50 ms, LV1RV–5 ms, VV_opt), where 50 ms is an exemplary value for the initial IED#2_max value and 5 ms is an exemplary offset value.

Thereafter, the device checks to see if the IED_max values are set too low and adjusts them upwardly, if needed. That is, at step 308, if IED#1_max is now zero (or negative), the device resets IED#1_max to 5 ms (or some other minimum value) and reduces IED#2_max by 5 ms (or some other suitable decrement value.) Likewise, at step 310, if IED#2_max is now zero (or negative), the device resets IED#2_max to 5 ms (or some other minimum value) and reduces IED#1_max by 5 ms (or some other suitable decrement value.) Having reset the values for IED#1_max and IED#2_max for either Seq#1 or Seq#2, the device then proceeds to the steps of FIG. 7 where the IED#1_max and IED#2_max values are used to limit the range of values for IED#1 and IED#2.

Figure 7:
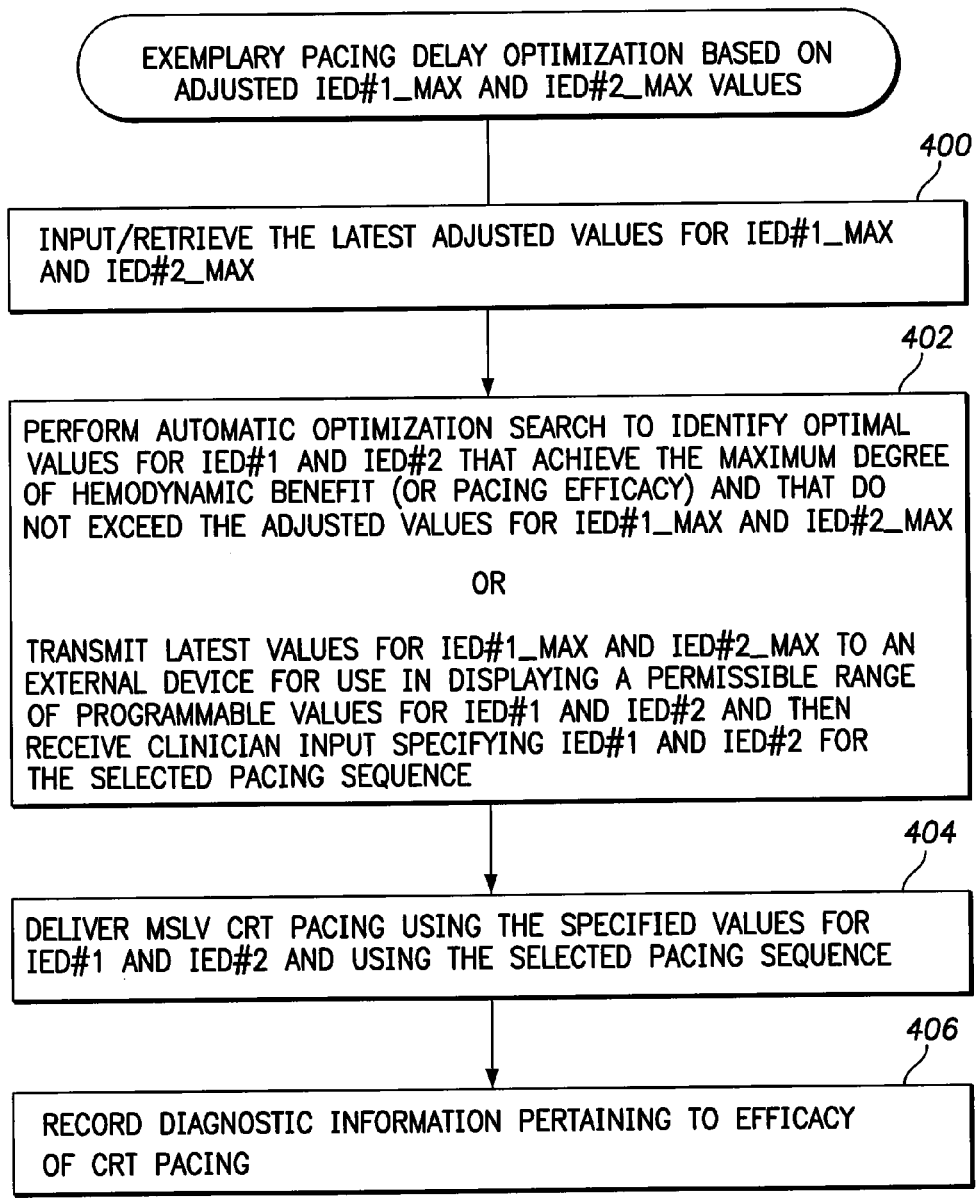
FIG. 7 is a flowchart exemplary techniques wherein MSLV pacing delays are optimized based on the maximum permissible delays determined by the methods of FIG. 3.

FIG. 7 illustrates the manner by which the device exploits the reset values for IED#1_max and IED#2_max. As already noted, these values are used to limit the range of programming of the IED#1 and IED#2 values. To this end, at step 400, the device inputs or otherwise retrieves the latest adjusted values for IED#1_max and IED#2_max values, i.e. the values set using the steps of FIG. 3 or 6. These values can be retrieved from memory, if stored therein, or input from an external device such as a device programmer. At step 402, the device performs an automatic optimization search to identify optimal values for IED#1 and IED#2 that do not exceed the adjusted values for IED#1_max and IED#2_max. This can involve delivering a series of test pacing pulses to the patient using various combinations of values for IED#1 and IED#2 while assessing a measure of cardiac performance or CRT efficacy. The values for IED#1 and IED#2 can be varied throughout a range of values that do not exceed IED#1 max and IED#2 max until a combination of IED#1 and IED#2 values are found that maximizes performance (based on whatever criteria is used to assess performance.) In some examples, physiological parameters representative of cardiac performance are measured, such as cardiac output (or surrogates) or stroke volume (or surrogates), to assess performance. Other parameters that can be used to assess pacing efficacy include one or more of: QRS duration; a degree of LV intracardiac electrogram fractionation; a degree of RV intracardiac electrogram fractionation; an activation time to non-paced sites in the LV; contractility or contractility surrogates; mechanical synchrony; and an activation time to non-paced sites in the RV.

See, for example, the optimization techniques described in U.S. patent application Ser. No. 12/607,817, of Ryu et al., filed Oct. 28, 2009, entitled "Systems and Methods for Optimizing Multi-Site Left Ventricular Pacing based on Interelectrode Conduction Delays," which describes systems and methods for determining preferred or optimal MSLV interelectrode pacing delays for use with MSLV pacing, particularly MSLV CRT. Other techniques described therein are directed to determining preferred or optimal combinations of LV electrodes or permutations of MSLV pacing vectors for use in delivering MSLV pacing using a multi-pole LV lead. See, also, U.S. patent applications Ser. Nos. 12/703,069 and 12/703,094, filed Feb. 9, 2010, of Rosenberg et al., entitled "Systems and Methods for Optimizing Multi-Site Cardiac Pacing and Sensing Configurations for use with an Implantable Medical Device." See, also, U.S. patent application Ser. No. 11/750,153, of Shelchuk, filed May 17, 2007, entitled "Expedited Set-Up of Multi-Electrode Lead (MEL)." See, also, U.S. Pat. No. 7,139,609 to Min et al., entitled "System and Method for Monitoring Cardiac Function via Cardiac Sounds using an Implantable Cardiac Stimulation Device." Additionally, see, U.S. patent application Ser. No. 11/416, 922, of Min et al., entitled "System and Method for Determining Optimal Pacing Stimulation Sites Based on ECG Information"; U.S. patent application Ser. No. 11/749,662, filed May 16, 2007, of Ryu et al., entitled "Adaptive Single Site and Multi-Site Ventricular Pacing"; U.S. patent application Ser. No. 12/507,679, of Min, filed Jul. 22, 2009, and entitled "Systems and Methods for Optimizing Ventricular Pacing Delays during Atrial Fibrillation"; and U.S. patent application Ser. No. 12/507,646, also of Min, filed Jul. 22, 2009, entitled "Systems and Methods for Optimizing Ventricular Pacing Delays for use with Multi-Pole Leads."

For techniques for assessing stroke volume, see, for example U.S. patent application Ser. No. 11/378,604, filed Mar. 16, 2006, of Kroll et al., entitled, "System and Method for Detecting Arterial Blood Pressure based on Aortic Electrical Resistance using an Implantable Medical Device." See, also, U.S. patent application Ser. No. 11/267,665, filed Nov. 4, 2005, of Kil et al., entitled "System and Method for Measuring Cardiac Output via Thermal Dilution Using an Implantable Medical Device with Thermistor Implanted in Right Ventricle." An integrated sensor providing a variety of sensor functions is described in U.S. patent application Ser. No. 11/927,026, filed Oct. 29, 2007, of Nabutovsky et al.

Alternatively, at step 402, the device transmits the latest values for IED#1_max and IED#2_max to an external device (such as device programmer) for use in displaying a permissible range of programmable values for IED#1 and IED#2 to a clinician or other user and then receive clinician input specifying IED#1 and IED#2. That is, the clinician selects the values for IED#1 and IED#2, subject to the maximum values specified by IED#1_max and IED#2_max. Also, even in cases where an automatic optimization procedure is used, the clinician is typically able to adjust or override the "optimal" values.

At step 404, the device then delivers MSLV CRT pacing using the specified values for IED#1 and IED#2 and using the previously selected pacing sequence. At step 406, the device records diagnostic information pertaining to efficacy of CRT pacing, such as any of the aforementioned hemodynamic efficacy parameters, which can be reviewed later by the clinician to verify that the MSLV CRT parameters have been properly and advantageously set.

As already noted, the aforementioned examples that provide for two programmable pacing sequences—SEQ 1 and SEQ 2—are merely illustrative. Additional or alternative sequences may be employed. Indeed, in some device platforms, six separate sequences are programmable.

For the sake of completeness, an exemplary pacer/ICD will now be described, which is equipped to perform CRT and includes components for performing the various functions and steps described above.

Exemplary Pacer/ICD

Figure 8:
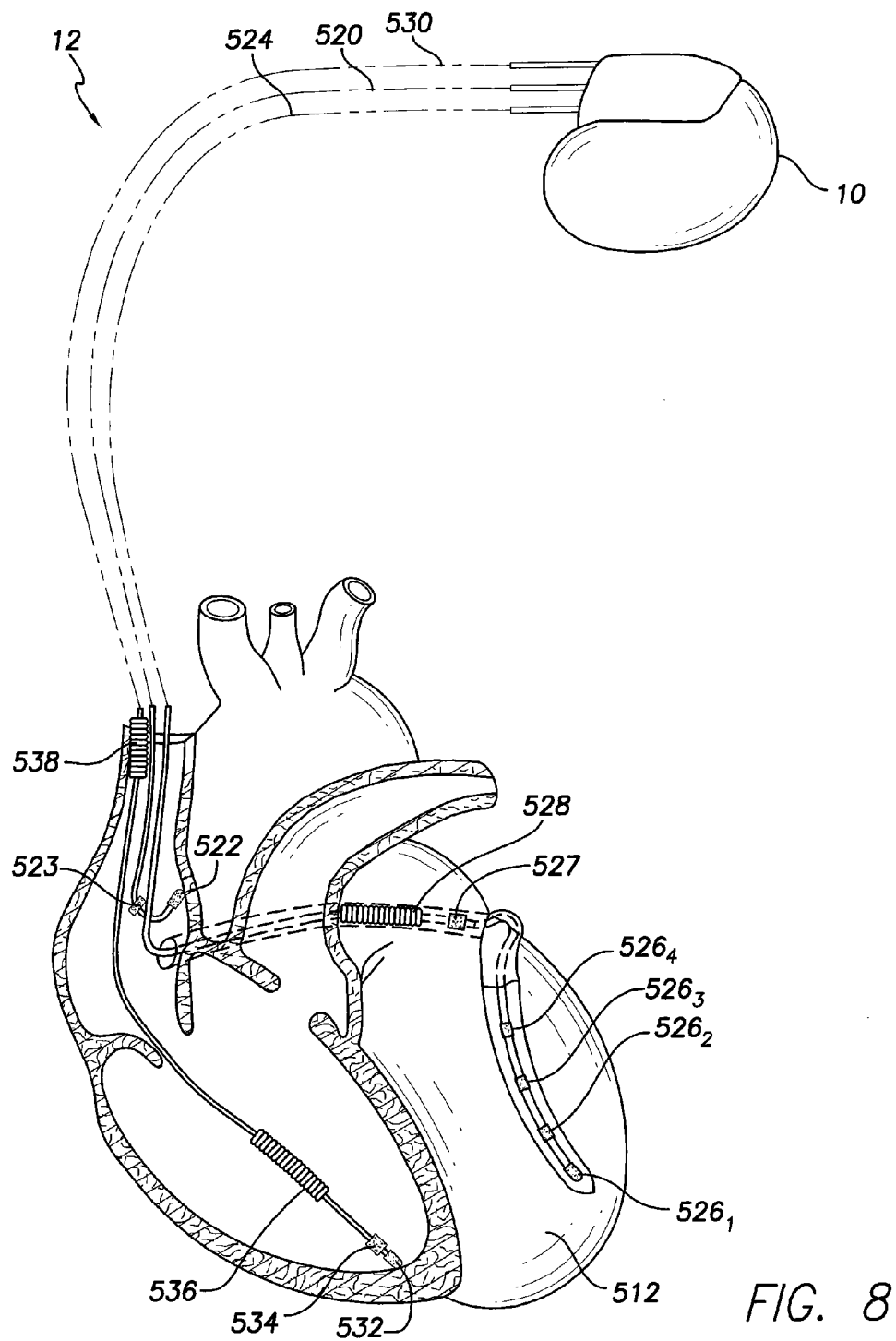
FIG. 8 is a simplified, partly cutaway view, illustrating the pacer/ICD of FIG. 1 along with at set of leads implanted into the heart of the patient.
Figure 9:
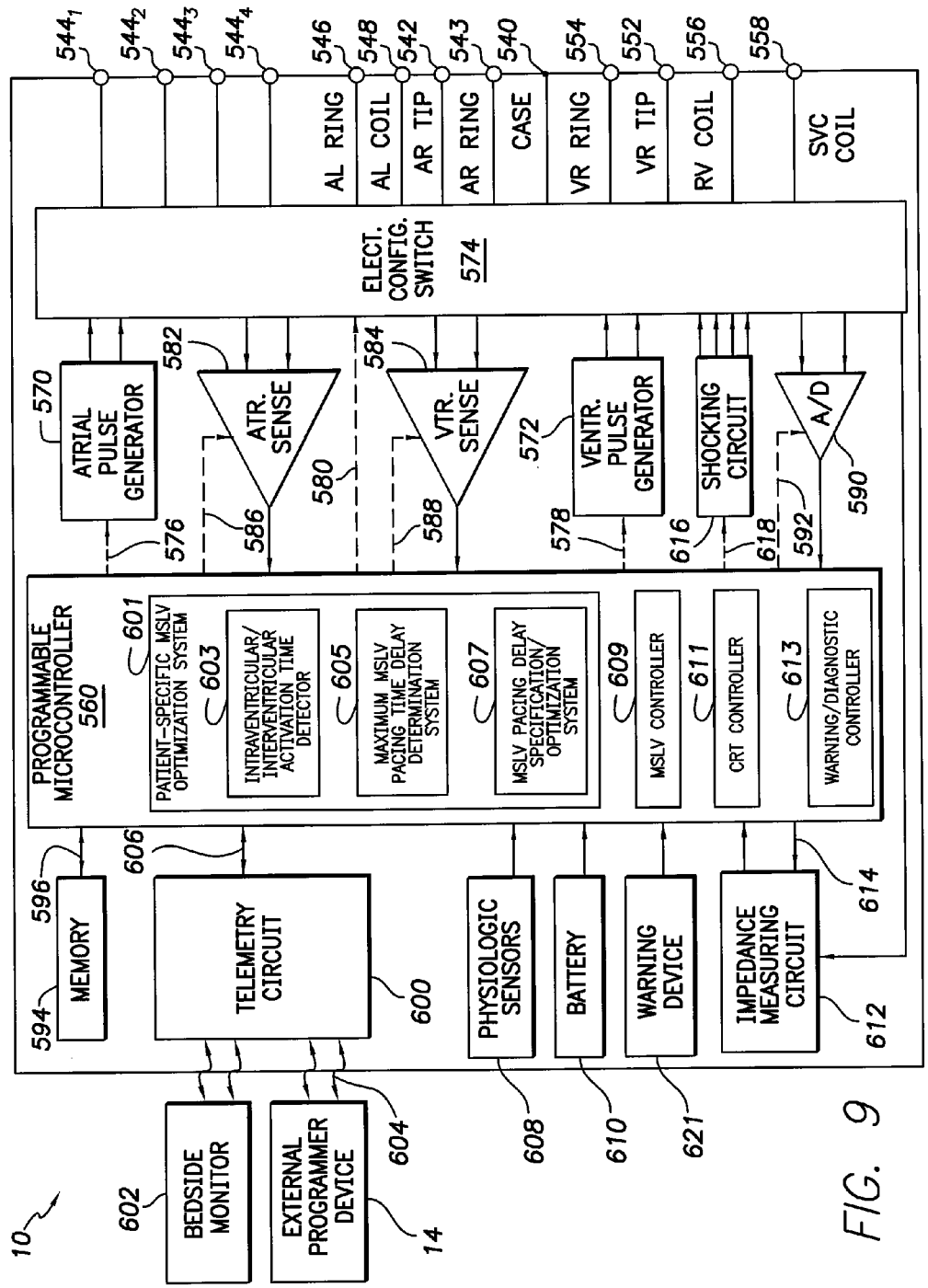
FIG. 9 is a functional block diagram of the pacer/ICD of FIG. 8, illustrating basic circuit elements that provide cardioversion, defibrillation and/or pacing stimulation in the heart an particularly illustrating an on-board components for performing the techniques of FIGS. 2-7.

With reference to FIGS. 8 and 9, a description of an exemplary pacer/ICD will now be provided. FIG. 8 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using MSLV pacing delays, as discussed above. To provide other atrial chamber pacing stimulation and sensing, pacer/ICD 10 is shown in electrical communication with a heart 512 by way of a left atrial lead 520 having an atrial tip electrode 522 and an atrial ring electrode 523 implanted in the atrial appendage. Pacer/ICD 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a multi-pole LV lead 524 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 524 is designed to receive atrial and ventricular cardiac signals and to deliver left ventricular pacing therapy using a set of four left ventricular electrodes $526_1$, $526_2$, $526_3$, and $526_4$ (thereby providing a quadra-pole lead), left atrial pacing therapy using at least a left atrial ring electrode 527, and shocking therapy using at least a left atrial coil electrode 528. The $526_1$ LV electrode may also be referred to as a "tip" or "distal" LV electrode. The $526_4$ LV electrode may also be referred to as a "proximal" LV electrode. In other examples, more or fewer LV electrodes are provided. Although only three leads are shown in FIG. 8, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 540 for pacer/ICD 10, shown schematically in FIG. 9, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, $544_1$-$544_4$, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes a left ventricular tip terminal ($VL_1$ TIP) $544_1$ and additional LV electrode terminals $544_2$-$544_4$ for the other LV electrodes of the quadra-pole LV lead.

The connector also includes a left atrial ring terminal ($A_L$ RING) 546 and a left atrial shocking terminal ($A_L$ COIL) 548, which are adapted for connection to the left atrial ring electrode 527 and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($V_R$ COIL) 556, and an SVC shocking terminal (SVC COIL) 558, which are adapted for connection to the right ventricular tip electrode 532, right ventricular ring electrode 534, the $V_R$ coil electrode 536, and the SVC coil electrode 538, respectively.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 9, an atrial pulse generator 570 and a ventricular pulse generator 572 generate pacing stimulation pulses for delivery by the right atrial lead 520, the right ventricular lead 530, and/or the LV lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry (not separately shown) used to control the timing of such stimulation pulses (e.g., pacing rate, AV delay, atrial interconduction (inter-atrial) delay, or ventricular interconduction (VV) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 582 and ventricular sensing circuits 584 may also be selectively coupled to the right atrial lead 520, LV lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 590. The data acquisition system 590 is configured to acquire intracardiac electrogram signals, convert the raw analog data into a digital signal, and store the digital signals for later processing and/or telemetric transmission to an external programmer 14 or a bedside monitor or personal advisory module (PAM) 602. The data acquisition system 590 is coupled to the right atrial lead 520, the LV lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with the external device 602, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of pacer/ICD 10 (as contained in the microcontroller 560 or memory 594) to be sent to the external device 602 through an established communication link 604. Pacer/ICD 10 further includes an accelerometer or other physiologic sensor 608, commonly referred to as a "rate-responsive" sensor because it is typically used to adjust pacing stimulation rate according to the exercise state of the patient. However, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV delay, VV delay, etc.) at which the atrial and ventricular pulse generators, 570 and 572, generate stimulation pulses. While shown as being included within pacer/ICD 10, it is to be understood that the physiologic sensor 608 may also be external to pacer/ICD 10, yet still be implanted within or carried by the patient. A common type of rate responsive sensor is an activity sensor incorporating an accelerometer or a piezoelectric crystal, which is mounted within the housing 540 of pacer/ICD 10. Other types of physiologic sensors are also known, for example, sensors that sense the oxygen content of blood, respiration rate and/or minute ventilation, pH of blood, ventricular gradient, stroke volume, cardiac output, contractility, etc.

The pacer/ICD additionally includes a battery 610, which provides operating power to all of the circuits shown in FIG. 9. The battery 610 may vary depending on the capabilities of pacer/ICD 10. If the system only provides low voltage therapy, a lithium iodine or lithium copper fluoride cell typically may be utilized. For pacer/ICD 10, which employs shocking therapy, the battery 610 should be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, appropriate batteries are employed.

As further shown in FIG. 9, pacer/ICD 10 is shown as having an impedance measuring circuit 612, which is enabled by the microcontroller 560 via a control signal 614. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 612 is advantageously coupled to the switch 674 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules or more), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

An internal warning device 621 may be provided for generating perceptible warning signals to the patient via vibration, voltage or other methods.

Insofar as MSLV pacing is concerned, the microcontroller includes a patient-specific MSLV optimization system 601 operative to perform or control at least some of the techniques of FIGS. 2-7, described above. The optimization system includes an intraventricular/interventricular activation time detector 603 operative to detect intraventricular and interventricular conduction delays for paced and sensed cardiac events. The system also includes a maximum pacing time delay determination system 605 operative to determine maximum permissible pacing time delays (such as the IED#1_max and IED#2_max values discussed above) for use with MSLV pacing, wherein the maximum pacing time delays are set based on the conduction delays to values sufficient to avoid capture problems due to wavefront propagation. Optimization system 601 also includes an MSLV pacing delay specification system 607 operative to set MSLV pacing delays (such as the IED#1 and IED#2 values discussed above) to values no greater than the maximum pacing delays. In implementations where the external device controls the optimization functions, these components might be omitted or might be configured to receive and process control parameters sent from the external device.

Additional components of the microcontroller include an MSLV controller 609 to control the actual delivery of MSLV pacing and a CRT controller 611 to control CRT, which can be performed in conjunction with MSLV pacing. A warning/diagnostics controller 613 controls the generation of warning signals, when needed, and the storing of diagnostic information and performance data within memory 594.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 10:
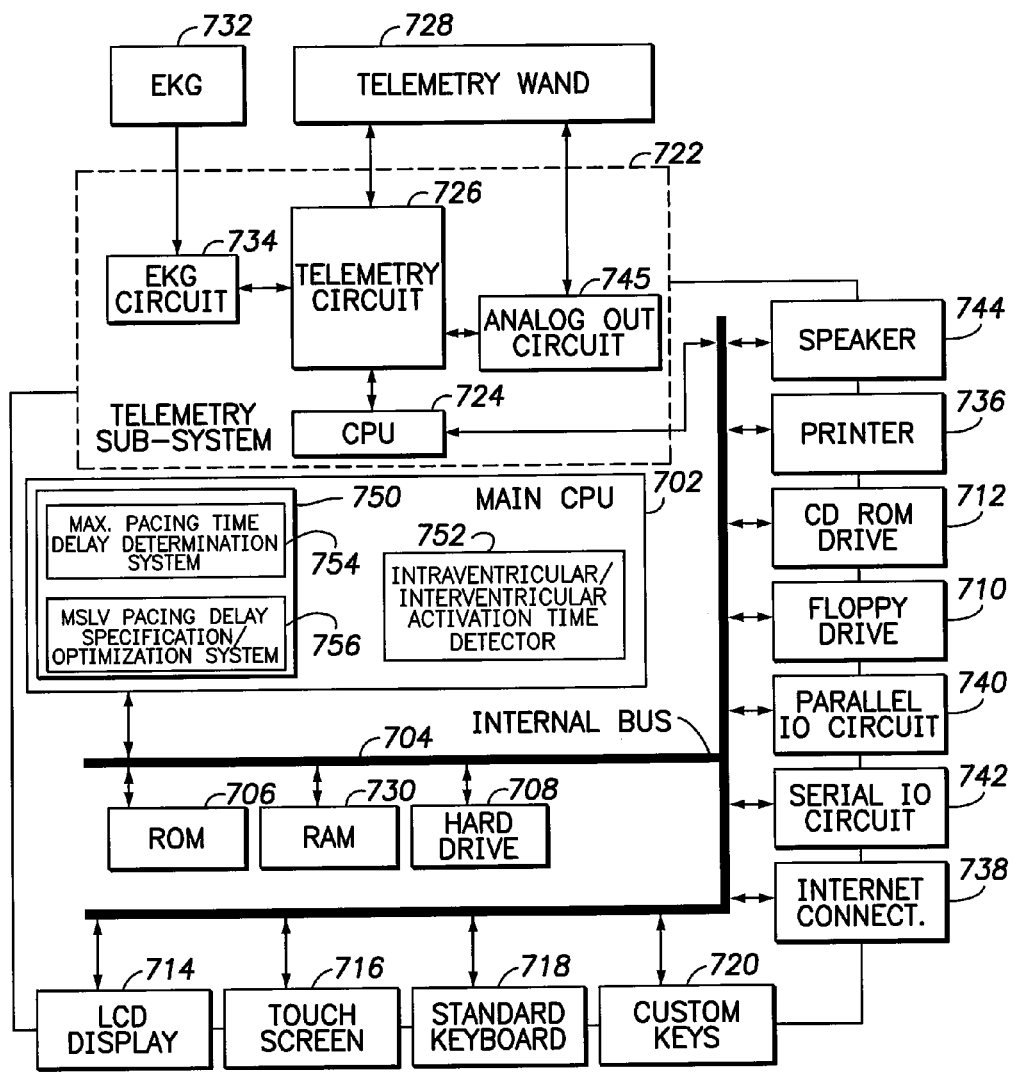
FIG. 10 is a functional block diagram illustrating components of the external device programmer of FIG. 1 and particularly illustrating programmer-based components for controlling the techniques of FIGS. 2-7.

FIG. 10 illustrates pertinent components of an external programmer 14 for use in programming the pacer/ICD of FIG. 9 and for performing/controlling the above-described optimization techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 702, which may be a generally programmable microprocessor or microcontroller or may be a dedicated processing device such as an application specific integrated circuit (ASIC) or the like. Software instructions to be performed by the CPU are accessed via an internal bus 704 from a read only memory (ROM) 706 and random access memory 730. Additional software may be accessed from a hard drive 708, floppy drive 710, and CD ROM drive 712, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 714 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 716 overlaid on the LCD display or through a standard keyboard 718 supplemented by additional custom keys 720, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 702 transmits appropriate signals to a telemetry subsystem 722, which provides components for directly interfacing with the implanted devices, and the EKG leads. Telemetry subsystem 722 includes its own separate CPU 724 for coordinating the operations of the telemetry subsystem. Main CPU 702 of programmer communicates with telemetry subsystem CPU 724 via internal bus 704. Telemetry subsystem additionally includes a telemetry circuit 726 connected to telemetry wand 728, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 734 for receiving surface EKG signals from a surface EKG system 732. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 730, hard drive 708 or within a floppy diskette placed within floppy drive 710. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 722 receives EKG signals from EKG leads 732 via an EKG processing circuit 734. As with data retrieved from the implanted device itself, signals received from the EKG leads are stored within one or more of the storage devices of the external programmer. Typically, EKG leads output analog electrical signals representative of the EKG. Accordingly, EKG circuit 734 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 702, the programming commands are converted to specific programmable parameters for transmission to the implanted devices via telemetry wand 728 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 736.

Additionally, CPU 702 also preferably includes an intraventricular/interventricular activation time detector 702 operative to detect intraventricular and interventricular conduction delays for paced and sensed cardiac events from within cardiac signals received from the implanted device. The CPU also includes a maximum pacing time delay determination system 754 operative to determine maximum permissible pacing time delays for use with MSLV pacing (such as the IED#1_max and IED#2_max values discussed above), wherein the maximum pacing time delays are set based on the conduction delays to values sufficient to avoid capture problems due to wavefront propagation. The CPU also includes an MSLV pacing delay specification/optimization system 756 operative to set MSLV pacing delays (such as the IED#1 and IED#2 values discussed above) to values no greater than the maximum pacing delays. The MSLV delays are then sent to the implanted device for use therein.

Depending upon the implementation, the various components of the CPU may be implemented as separate software modules or the modules may be combined to permit a single module to perform multiple functions. In addition, although shown as being components of the CPU, some or all of these components may be implemented separately using ASICs or the like.

Programmer/monitor 14 also includes an internet connection component 738 to permit direct transmission of data to other programmers via the public switched telephone network (PSTN) or other interconnection line, such as a T1 line or fiber optic cable or via wireless systems. Depending upon the implementation, the internet connection may be connected directly to internal bus 704 may be connected to the internal bus via either a parallel port 740, a serial port 742 or other device. Other peripheral devices may be connected to the external programmer via parallel port 740 or a serial port 742 as well. Although one of each is shown, a plurality of input output (IO) ports might be provided. A speaker 744 is included for providing audible tones to the user, such as a warning beep in the event improper input is provided by the physician. Telemetry subsystem 722 additionally includes an analog output circuit 745 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted device and to reprogram the implanted device if needed. The descriptions provided herein with respect to FIG. 10 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable cardiac stimulation device equipped for multi-site left ventricular (MSLV) pacing using a multi-pole LV lead in combination with an RV lead, the method comprising:
    detecting intraventricular and interventricular conduction delays for paced cardiac events;
    determining maximum pacing time delays for use with MSLV pacing, wherein the maximum pacing time delays are set, based on the conduction delays, to values sufficient to avoid capture problems due to wavefront propagation;
    setting MSLV pacing time delays to values no greater than the maximum pacing delays; and
    controlling the delivery of ventricular pacing to deliver a set of pulses using the MSLV pacing delays;
    wherein the device accommodates two programmable MSLV delays (IED#1 and IED#2);
    wherein the device is programmed to apply a first MSLV pacing sequence (Seq#1) wherein an RV pulse is followed by an LV1 pacing pulse and then by an LV2 pacing pulse, wherein LV1 represents a first LV pacing site, LV2 represents a second LV pacing site, and a first pacing delay (IED#1) is applied between the RV and LV1 pulses and a second pacing delay (IED#2) is applied between the LV1 and LV2 pulses.

2. The method of claim 1 wherein the maximum pacing time delays are set to values sufficient to avoid lack of capture and fusion caused by propagating wavefronts from other pacing sites.

3. The method of claim 1 further comprising:
measuring a first paced interventricular conduction delay (RVLV1) within the patient, wherein the first delay (IED#1) is set no greater than a maximum programmable first delay (IED#1_max) and, wherein the maximum programmable first delay IED#1_max is set to the lesser of an initial IED#1_max value and the first paced interventricular conduction delay (RVLV1).

4. The method of claim 3 further comprising:
measuring a paced intraventricular conduction delay (LVLV) within the patient, wherein the second delay (IED#2) is set no greater than a maximum programmable second delay (IED#2_max), wherein the maximum programmable second delay (IED#2_max) is set to the lesser of an initial IED#2_max value and the paced intraventricular conduction delay (LVLV).

5. The method of claim 4 wherein IED#1_max is set to Min(initial IED#1_max, RVLV1—a fusion avoidance offset).

6. The method of claim 5 wherein IED#2_max is set to Min(initial IED#2_max, LVLV—the fusion avoidance offset).

7. The method of claim 1 wherein the device is programmed to apply a second MSLV pacing sequence (Seq#2) wherein an LV1 pulse is followed by an LV2 pacing pulse and then by an RV pacing pulse, wherein a first pacing delay (IED#1) is applied between the LV1 and LV2 pulses and a second pacing delay (IED#2) is applied between the LV2 and RV pulses.

8. The method of claim 7 further comprising:
measuring a paced intraventricular conduction delay (LVLV) within the patient, wherein the first delay (IED#1) is set no greater than a maximum programmable first delay (IED#1_max), wherein the maximum programmable first delay (IED#1_max) is set to the lesser of an initial IED#1_max value and the paced intraventricular conduction delay (LVLV).

9. The method of claim 1 wherein the setting the MSLV pacing delays includes performing an optimization search to identify preferred values for the MSLV pacing delays within a range of values no greater than the maximum MSLV pacing delays.

10. The method of claim 1 wherein the setting the MSLV pacing delays includes inputting user-specified values for the MSLV pacing delays from within a range of values no greater than the maximum MSLV pacing delays.

11. The method of claim 1 wherein the implantable device is configured to be used in conjunction with an external system and wherein at least some of the steps are performed by the external system.

12. The method of claim 1 wherein the implantable device is configured to be used in conjunction with an external system and wherein at least some of the steps are performed by the implantable device.

13. A system for use with an implantable cardiac stimulation device equipped for multi-site left ventricular (MSLV) pacing using a multi-pole LV lead in combination with an RV lead, the system comprising:
an intraventricular/interventricular activation time detector configured to detect intraventricular and interventricular conduction delays for paced cardiac events;
a maximum MSLV pacing time delay determination system configured to determine maximum pacing time delays for use with MSLV pacing, wherein the maximum pacing time delays are set based on the conduction delays to values sufficient to avoid capture problems due to wavefront propagation;
an MSLV pacing delay specification system configured to set MSLV pacing delays to values no greater than the maximum pacing time delays; and
an MSLV controller configured to control delivery of ventricular pacing to deliver a set of pulses using the MSLV pacing delays;
wherein the MSLV pacing delay specification system accommodates two programmable MSLV delays (IED#1 and IED#2);
wherein the MSLV controller is programmed to apply a MSLV pacing sequence including an RV pacing pulse, an LV1 pacing pulse, and an LV2 pacing pulse, wherein LV1 represents a first LV pacing site and LV2 represents a second LV pacing site, and a first pacing delay (IED#1) is applied between a first pair of pulses in the MSLV pacing sequence and a second pacing delay (IED#2) is applied between a second pair of pulses in the MSLV pacing sequence.

14. A system for use with an implantable cardiac stimulation device equipped for multi-site left ventricular (MSLV) pacing using a multi-pole LV lead in combination with an RV lead, the system comprising:
means for detecting intraventricular and interventricular activation times for paced cardiac events;
means for determining maximum pacing time delays for use with MSLV pacing, wherein the maximum pacing time delays are set based on the conduction delays to values sufficient to avoid capture problems due to wavefront propagation;
means for setting MSLV pacing delays to values no greater than the maximum pacing time delays; and
means for controlling delivery of ventricular pacing to deliver a set of pulses using the MSLV pacing delays;
wherein the means for setting MSLV pacing delays accommodates two programmable MSLV delays (IED#1 and IED#2);
wherein the means for controlling delivery is programmed to apply a MSLV pacing sequence including an RV pacing pulse, an LV1 pacing pulse, and an LV2 pacing pulse, wherein LV1 represents a first LV pacing site and LV2 represents a second LV pacing site, and a first pacing delay (IED#1) is applied between a first pair of pulses in the MSLV pacing sequence and a second pacing delay (IED#2) is applied between a second pair of pulses in the MSLV pacing sequence.

* * * * *